United States Patent [19]

Knobloch et al.

[11] 4,022,817

[45] May 10, 1977

[54] ESTERS PREPARED FROM DIACYLIUM COMPLEXES OF TETRAHALOTEREPHTHALIC ACID

[75] Inventors: James O. Knobloch, Naperville, Ill.; Fausto Ramirez, Goshen, Va.

[73] Assignee: Standard Oil Company (Indiana), Chicago, Ill.

[22] Filed: Sept. 15, 1975

[21] Appl. No.: 613,472

Related U.S. Application Data

[62] Division of Ser. No. 477,668, June 10, 1974, Pat. No. 3,953,481.

[52] U.S. Cl. .................. 260/475 R; 260/45.7 R; 260/45.85 S; 260/75 H; 260/78 R; 260/78.41; 260/475 N; 260/475 P; 260/475 PN; 260/515 A; 260/544 D; 260/544 F; 260/544 P; 260/558 R; 526/293
[51] Int. Cl.$^2$ .................. C07C 67/00; C07C 69/76
[58] Field of Search ..... 260/475 P, 475 R, 475 PN, 260/475 N, 475 F

[56] References Cited

OTHER PUBLICATIONS

Newman, J.A.C.S., 63, pp. 2431–2435 (1941).

Primary Examiner—Jane S. Myers
Attorney, Agent, or Firm—William H. Magidson; Arthur G. Gilkes; William T. McClain

[57] ABSTRACT

Diacylium complexes of tetrahaloterephthalic acid can be produced by reacting tetrahaloterephthalic acid with sulfur trioxide to form compounds capable of reacting with various nucleophilics.

7 Claims, No Drawings

ESTERS PREPARED FROM DIACYLIUM COMPLEXES OF TETRAHALOTEREPHTHALIC ACID

This is a division of application Ser. No. 477,668 filed 6/10/74, now U.S. Pat. No. 3,953,481.

This invention relates to diacylium complexes of a tetrahaloterephthalic acid and derivatives thereof.

It is generally recognized that the acid groups of tetrahaloterephthalic acids are sterically hindered, thereby making it difficult to produce tetrahaloterephthalic acid derivatives. This is unfortunate since the diesters of these acids are useful as fire-retardant plasticizers of resinous polymers of vinyl chloride. Further, these acids are potentially useful in the production of fire-retardant polyesters, polyamides, etc. Accordingly, it is desirable to provide more reactive forms of the tetrahaloterephthalic acids.

The general objective of this invention is to provide tetrahaloterephthalic compounds having highly reactive acid groups. Another object of this invention is to provide a new method of producing diesters of tetrahaloterephthalic acid. A further object is to provide another method of producing polytetrahaloterephthalic anhydrides. Other objects appear hereinafter.

We have now found that tetrahaloterephthalic acids can be converted into highly reactive forms by producing diacylium complexes. The diacylium complexes are very reactive and can be used to produce (1) esters by reacting with monohydroxy compounds, (2) amides by reacting with amines, (3) acyl halides by reacting with halosulfonic acids, (4) polyanhydrides by heating alone or together with polycarboxylic acids, (5) polyesters by reacting with glycols, (6) polyamides by reacting with diamines, etc.

The diacylium complexes of this invention can be represented by the structure

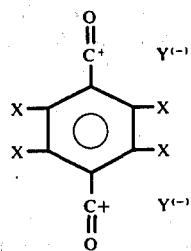

wherein X is a halogen and Y is an anion such as $HSO_4^-$, $H_2S_2O_7^-$, etc.

These complexes can be formed by reacting the free acids with sulfur trioxide in the substantial absence of other compounds containing active Zerewitinoff hydrogen groups thereby forming diacylium sulfate (bis-bisulfates, pyrosulfates, etc.) complexes of the acids. The diacylium complexes do not form in the presence of compounds having active Zerewitinoff hydrogen groups. Although the tetrahaloterephthalic acids are relatively insoluble in sulfur trioxide, the reaction proceeds very smoothly. For example, when white granular tetrahaloterephthalic acid is added to liquid sulfur trioxide, the tetrahaloterephthalic acid turns bright red, as acid dissolves forming the diacylium complex. After a few minutes, an insoluble gold underlayer forms with a yellowish green top layer. On heating or by extended contact at room temperature, the gold underlayer gets thicker as more of the diacylium complex, which is relatively insoluble in sulfur trioxide, precipitates.

The ease with which these complexes form is surprising since it is generally recognized that treatment or organic compounds with substantially pure sulfur trioxide leads to charring of the organic compounds. See, for example, du Pont trade literature on sulfonating-sulfating agents, their characteristics and uses wherein du Pont indicates that "undiluted liquid sulfur trioxide reacts so exothermically and fast that charring occurs with all but the most stable organic compounds." To avoid charring, sulfur trioxide is normally employed as oleum or in a complex. However, in the processes of the present application, it is unnecessary and undesirable to employ the sulfur trioxide in complexes or as oleum.

Suitable tetrahaloterephthalic acids useful in this invention include tetrachloroterephthalic acid, tetrabromoterephthalic acid, chlorotribromoterephthalic acid, 2,5-dibromo-3,6-dichloroterephthalic acid, trichlorobromoterephthalic acid, trichlorofluoroterephthalic acid, trifluorobromoterephthalic acid, etc.

In somewhat greater detail the diacylium sulfate complexes of this invention are produced by dispersing the tetrahaloterephthalic acid in substantially pure sulfur trioxide or in mixtures of sulfur trioxide and sulfur dioxide diluent in the absence of Zerewitinoff hydrogen atoms other than those provided by the organic acids. The sulfur trioxide must be present in a concentration of at least 2 moles per mole of tetrahaloterephthalic acid. Generally, the sulfur trioxide is in a substantial molar excess. When approximately a 2:1 molar ratio is employed, bisulfate counter ions are produced. When a 4:1 molar ratio is employed, pyrosulfate counter ions are produced. At higher ratios of sulfur trioxide to tetrahaloterephthalic acid, more complicated counter ions are produced. The composition is then heated to 40°–50° C. for a short time to stabilize the complex. Alternatively the composition can be stirred at room temperature for 45 minutes or so to stabilize the complex. If the complex is not completely formed (stabilized), either very low or no yield of desired product is realized on subsequent addition of reactive nucleophilic.

If excess sulfur trioxide over that necessary to form counter ions is used to produce the complexes, the excess is preferably separated from the complex for economy and to prevent any undesirable charring in subsequent reactions of the diacylium complexes. The excess sulfur trioxide can be removed from the solid diacylium complexes by distillation or extracting with inert liquids, such as fluorocarbons, sulfur dioxide, etc. The diacylium complexes of tetrachloro and tetrabromoterephthalic acid have an infrared absorption frequency at about 2240 to 2250 cm$^{-1}$.

Although the preferred method of producing diacylium complexes of tetrahaloterephthalic acids comprises the reaction of sulfur trioxide with tetrahaloterephthalic acids, it is also possible to produce diacylium complexes from the corresponding tetrahaloterephthalolyl fluorides by reacting the tetrahaloterephthalolyl fluorides with antimony pentafluoride. In this case, the infrared absorption frequency is also in the range of about 2240 to 2250 cm$^{-1}$. However, this latter method of producing diacylium complexes is economically unattractive from the point of view that it is necessary to convert the tetrahaloterephthalic acids to the tetrahaloterephthalolyl fluorides, followed by reaction with the antimony pentafluoride. On the other hand, it is substantially cheaper and simpler to produce the diacylium complexes directly from the free acids and sulfur trioxide.

The diacylium complexes of this invention can be converted to polyester plasticizers by reacting the diacylium compounds at a temperature of −15° C. to about 100° C. with excess monohydroxy compounds. Suitable monohydroxy compounds include alcohols containing from 1 to 24 carbon atoms such as methyl alcohol, ethyl alcohol, isopropyl alcohol, allyl alcohol, methallyl alcohol, n-butyl alcohol, n-hexyl alcohol, n-octyl alcohol, 2-ethyl-hexyl alcohol, decyl alcohol, tridecyl alcohol, stearyl alcohol, oleyl alcohol, tetracosyl alcohol, aromatic hydroxy compounds containing 6 to 24 carbon atoms, such as phenol, cresol, parastearyl phenol, naphthol, etc. In general, the reaction vessel should contain from about 1 to 10 moles of monohydroxy compound per carboxyl equivalent in the diacylium compound in order to form diesters.

The simple esters of tetrahaloterephthalic acid can be used as fire-retardant plasticizers in a concentration of from about 5 to 200 parts by weight per 100 parts by weight resinous polymer of vinyl chloride. These plasticizers may be used as the sole plasticizers, two or more esters of tetrahaloterephthalic acid may be employed together or alternatively, these esters may be used in conjunction with other conventional plasticizers. Suitable resinous polymers of vinyl chloride include homopolymers of vinyl chloride, copolymers of vinyl chloride and vinyl acetate, such as the conventional 95–5 vinyl chloride/vinyl acetate copolymers, partially hydrolyzed vinyl chloride/vinyl acetate copolymers, etc.

The diacylium compounds can also be converted to polyesters by reacting the diacylium compounds with substantially equal molar quantities of dihydric alcohols, such as ethylene glycol, propylene glycol, 1,6-hexane diol, etc., or to polyamides by reacting the diacylium compounds with diamines such as hexamethylene diamine, etc.

The diacylium complexes are particularly useful for the production of stable linear polytetrahaloterephthalic anhydrides, which are the subject of copending application Ser. No. 434,953, filed about Jan. 21, 1974 in the name of Knobloch. As pointed out in Ser. No. 434,953, the anhydride linkages of the polytetrahaloterephthalic anhydrides are stable even when the polymers are refluxed in aqueous alkali.

The polyanhydrides can be produced by (1) heating the polytetrahaloterephthalic acid with sulfur trioxide in liquid sulfur dioxide under pressure thereby generating the diacylium complex in situ and continuing the reaction until the polyanhydride is formed, (2) heating the unstabilized diacylium complex in liquid sulfur dioxide thereby stabilizing the complex and continuing the reaction until the polyanhydride is formed or, (3) heating the stabilized diacylium complex in sulfur dioxide under pressure.

Polyanhydrides composed of only tetrahaloterephthalic acids are relatively infusible and solvent insoluble. The tetrahaloterephthalic acids can be polymerized with other dicarboxylic acids to improve their plasticity or other physical properties. In general; the tetrahaloterephthalic acids should comprise at least 50 mole percent of the polyanhydride in order to maintain the stability of the anhydride linkage during subsequent processing of the polyanhydride. Suitable comonomers include aromatic dicarboxylic acids, such as terephthalic acid, isohthalic acid, 2,5-dibromoterephthalic acid, phthalic acid, 2,6-naphthalenedicarboxylic acid, etc.; aliphatic dicarboxylic acids such as adipic acid, glutaric acid, sebacic acid, hexafluoroglutaric acid, octafluoroadipic acid, etc.

Irrespective of the method of generating the stabilized diacylium complex, the polyanhydrides are formed by heating the diacylium complex dissolved in liquid sulfur dioxide under pressure. The weight ratio of tetrahaloterephthalic acid compound to sulfur dioxide can range from about 1 to 25 parts by weight, and preferably 3 to 20 parts by weight, per 100 parts by weight sulfur dioxide. The sulfur trioxide should be present in a ratio of 0.5 to 10 moles per mole acid, preferably 1 to 3. However, the yield of polyanhydride tends to drop as the mole ratio of sulfur trioxide to acid goes above 1:1. For example, there is 69% yield at a 1:1 ratio of sulfur trioxide to tetrabromoterephthalic acid, a 59% yield at 2:1 and 23% yield at 4:1.

The concentration of sufur trioxide to acid compound can be easily adjusted by dispersing the tetrahaloterephthalic acid in at least two moles sulfur trioxide per mole tetrahaloterephthalic acid, to form the unstabilized complex. The excess sulfur trioxide is removed by dispersing the sulfur trioxide-tetrahaloterephthalic acid in a perfluorohydrocarbon, such as Freon 113 (1,1,2-trichlorotrifluoroethane), and partitioning insoluble reaction product. This reaction product and approximately 0.5 to 2.0 moles of dicarboxylic acid are dispersed in liquid sulfur dioxide to provide approximately 0.66 to 1.33 moles sulfur trioxide per mole of dicarboxylic acid. While this method is convenient for producing copolymeric polyanhydrides in good yields, the polymers are generally of somewhat lower molecular weight and contain about 8 to 15 anhydrides moieties.

The reaction can be carried out at 40° to 150° C., preferably 100° to 135° C. under sufficient pressure to dissolve the acid in the sulfur dioxide. Under these conditions, the reaction is relatively rapid and polymerization can be completed in 1/4 to 2 hours.

The polyanhydrides, which have

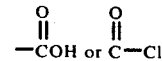

end groups, can be isolated by distilling off sulfur dioxide, partitioning off insoluble polyanhydride and washing out impurities by conventional means, e.g., by dissolving sulfur reaction product and unreacted acid in water and methanol and partitioning the insoluble polyanhydride.

The tetrahaloterephthalic anhydride polymers, produced by any route, can be blended with a suitable flammable polymer, preferably a thermoplastic addition polymer, to impart the desired degree of fire retardancy. Suitable thermoplastic addition polymers include homopolymers, copolymers, block copolymers, etc., of olefins, such as ethylene, proylene, styrene, vinyl toluene; methyl methacrylate; ethyl acrylate; vinyl chloride; vinyl bromide; acrylonitrile; butadiene; etc. As indicated above, the polytetrahaloterephthalic anhydride should comprise a minor amount of the composition (less than 50% by weight down to about 0.5% by weight). The concentration of polyanhydride should be adjusted to provide the desired degree of fire retardancy. For example, compositions comprising 85% by weight of either polystyrene or polypropylene and 15% by weight tetrabromoterephthalic anhydride have an SE-0 or SE-1 rating. The compositions contain about 10.3% by weight bromine.

The following examples are merely illustrative:

EXAMPLE I

Four grams tetrabromoterephthalic acid was suspended in 396g sulfur trioxide and brought to a boil with stirring over a one hour period to stabilize the diacylium complex. A golden lower liquid layer developed. After cooling to 25° C., the upper sulfur trioxide phase was decanted leaving 17.5g of under layer. The under layer was washed four times by suspending in 50 ml portions of Freon 113 and decanting to remove dissolved sulfur trioxide. The washed diacylium sulfate complex weighed 7.6g.

The diacylium complex was added to 425 ml absolute methanol with stirring. About 300 ml of methanol was distilled and the residual solution was cooled to 25° C. A crystalline solid product was recovered by filtration. The filter cake was washed with 10 ml methanol and dried to give dimethyl tetrabromoterephthalate (1.8g), mp 207°–210° C. Ir confirmed the identity of the diester. A gas chromatogram showed only one peak at the correct retention time.

EXAMPLE II

This example illustrates that the diacylium complex must be stabilized prior to reaction with alcohols in order to produce diesters. Two and three-hundredths grams tetraromoterephthalic acid was stirred in 25 ml sulfur trioxide at 25° C. for 5 minutes under a dry $N_2$ atmosphere. Then 50 ml of Freon 113 (1,1,2-trifluoro-1,2,2-trichloroethane) was added to the suspension, which was stirred and allowed to settle. The Freon-$SO_3$ liquid was decanted. Four additional 25 ml portions of Freon 113 was successively used to extract more $SO_3$ from the residue. Methanol 25 ml) was then added to the unstabilized yellow-green residue. The color was immediately discharged and a white suspension resulted. After refluxing 15 minutes (with some loss of solvent) the suspension (21g) was diluted with 50 ml water. After cooling in an ice bath the solids were filtered. The filter cake was dried and weighed (1.70g). An ir spectrum (KBr disc) showed the product to be tetrabromoterephthalic acid ($Br_4TA$) with a very small amount of the polyanhydride of $Br_4TA$. No diester was formed.

EXAMPLE III

This example illustrates that a stabilized diacylium complex cannot be formed in oleum containing 30.3% sulfur trioxide. Twenty ml oleum (30.3% $SO_3$ and 69.7% $H_2SO_4$) was added to 1.0 grams tetrabromoterephthalic acid. The flask was closed to protect it from moisture and heated on a water bath to 56° C. to get the tetrabromoterephthalic acid completely in solution. The solution was added dropwise with stirring to 200 ml absolute methanol. The methanol caused a vigorous reaction and the final temperature was 43° C. Most of the alcohol was distilled under vacuum (42° C. max. water bath temperature and 2-5mm Hg pressure), interrupting the distillation to add 100 ml water. The suspension remaining was filtered and the cake was washed with 10 ml water. After drying, the cake weighed 0.9g. A gas chromatogram showed no dimethyl ester. An ir spectrum showed that the sample was tetrabromoterephthalic acid.

EXAMPLE IV

This example illustrates the production of the dimethyl ester of tetrachloroterephthalic acid from the stabilized diacylium sulfate complex of tetrachloroterephthalic acid. Nine-tenths grams tetrachloroterephthalic acid was added to 86g sulfur trioxide in an Erlenmeyer flask covered with a watch glass. The bright yellow suspension was heated and after 15 minutes became cloudy yellow with green solids coming out of solution. After one hour (about 20 minutes at boiling) the stabilized diacylium complex was allowed to cool to room temperature. The yellow $SO_3$ upper layer was decanted from the greenish yellow solids. The solids were cautiously added to methanol and allowed to stir. A crystalline product precipitated from solution. It was filtered off, shaken with water and dried to give dimethyl tetrachloroterephthalate (0.3g), m.p. 152°–154½° C. (lit. m.p. 154°–155° C.) with an ir spectrum (KBr) identical to the dimethyl ester made by reacting $Cl_4TA$ with diazomethane.

EXAMPLE V

This example illustrates the production of tetrabromoterephthaloylchloride from the stabilized diacylium complex. One gram of tetrabromoterephthalic acid was dissolved in 33 ml liquid sulfur trioxide and stirred for one hour in a closed flask at room temperature. The initial deep red changed to pale yellow after stirring for 15 minutes and diacylium complex started to come out of solution. The complex was stabilized by distilling excess sulfur trioxide at 300 to 360 mm Hg pressure using a water bath at 46° C. The sulfur trioxide distilled over at 44° to 46° C. Fifteen ml chlorosulfonic acid was added to the 6.7g of diacylium residue from the distillation and stirred overnight. The solution was transferred to a separatory funnel and extracted with one 30 ml and two 20 ml portions carbon tetrachloride. The combined carbon tetrachloride extracts were distilled and chlorosulfonic acid removed under vacuum. The final residue was sublimed at 280° C., 10 mm Hg yielding 0.4 grams tetrabromoterephthalolyl chloride. A gas chromatogram of the sublimate showed only two peaks in about the relative amounts of 99.9% tetrabromoterephthalolyl chloride and 0.1% unknown. The product melted sharply at 199.5°–200.5° C.

Essentially the same results can be obtained using other halo-sulfonic acids (e.g., fluorosulfonic acid).

EXAMPLE VI

This example illustrates the production of a stable diacylium complex by stirring at room temperature followed by reaction with chlorosulfonic acid to form tetrachloroterephthalolyl chloride. Three grams of tetrachloroterephthalic acid was stirred in 150 ml sulfur trioxide for 54 minutes at room temperature (ca 25° C.) to stabilize the complex. The suspension was then diluted with 100 ml Freon 113. The liquid phase was decanted. The solids were extracted successively with four 50 ml portions Freon 113 to remove excess $SO_3$. Then 25 ml of chlorosulfonic acid was added to partially dissolve the solids. The suspension was stirred 80 minutes and then extracted with five 50 ml portions of carbon tetrachloride. The $CCl_4$ and small amount of dissolved ($ClSO_3H$ were distilled under vacuum (final bath temperature was 90° C. and absolute pressure was ca 1 mm Hg). The 2.3 g residue was sublimed at 182°–194° C. bath temperature (1 mm Hg) to give 2.1 g sublimate and 0.2 g residue. The sublimate melted 141½°–144° C. and was 99.2 wt. % pure tetrachloroterephthaloyl chloride by bas chromatography using an internal standard. An infrared spectrum further confirmed the product identity. This yield is 62 mole % based on Cl$_4$TA charged.

EXAMPLE VII

This example illustrates the production of polytetrachloroterephthalic anhydride from a diacylium complex where the complex is stabilized in situ without isolation of the stabilized complex. Nine and forty-five hundredth grams of tetrachloroterephthalic acid was added to an open, dry 300 ml Hastelloy C autoclave together with 1.29 ml of sulfur trioxide (about 2.49 grams) and the autoclave was closed. One hundred thirty-six grams of liquid sulfur dioxide was pressured into the autoclave after it had been pressure tested with nitrogen and vented. The autoclave temperature was raised to 120° C. (575 psig) over the period of one hour while stirring at 2100 r.p.m. and then held in a range of 123° to 129° C. (614–617 psig) for 90 minutes. The next day, the autoclave was opened and about 95 ml of a gray, smooth suspension was poured out. The sulfur dioxide was permitted to evaporate and the residue was dispersed in 400 ml of water and digested for three hours on a steam bath. After cooling, the insoluble polymer was filtered, washed with three 45 ml portions of water and dried. The dry polymer weighed 7.10 grams. A 4.95 gram sample of the crude polytetrachloroterephthalic acid anhydride was refluxed in 80 ml methanol for four hours, cooled, filtered and washed with 50 ml methanol. Dry polymer weighing 1.88 grams was isolated. The infrared spectrum showed absorptions at 1820, 1763, 1170 and 1000 cm$^{-1}$. The acid number of the polyanhydride was 13 mg. of KOH per gram, indicating an average molecular weight of 8,640 and a polymer chain of 30.1 tetrachloroterephthalic acid anhydride moieties. The product analyzed 49.1% chlorine.

EXAMPLE VIII

This example illustrates the production of a polytetrahaloterephthalic anhydride copolymer from a mixture of unstabilized diacylium complex and free acid where the diacylium complex is stabilized in situ. Three and one half grams of tetrabromoterephthalic acid was pleased in an autoclave with 25 ml of sulfur trioxide and stirred for five minutes. Excess sulfur trioxide was removed with one 110 ml and four 50 ml portions of Freon 113, leaving the unstabilized diacylium complex in the reactor. Then 4.4 grams of tetrachloroterephthalic acid and 139 grams of sulfur dioxide was added to the autoclave. The reaction was carried out with stirring (2,000 to 2,200 r.p.m.) in an autoclave at 124° C. (62 to 649 psig) for 70 minutes. The next day, the reactor was chilled and opened under nitrogen. A graytan suspension of polymer was poured out and after the sulfur dioxide was evaporated, the residue was digested with 280 ml of water on the steam bath for 75 minutes. The cooled suspension was filtered, washed with two 30 ml portions of water and dried, yielding a cake weighing 6.0 grams. All of the product was refluxed with 100 ml of absolute methanol for 3½ hours, cooled to room temperature, filtered and washed with two 25 ml portions of methanol. The dried cake weighed 3.4 grams. The heteropolymer had an infrared spectrum which indicated a mixed anhydride showing absorption at 1820, 1785 and 1763, 1170, 1145, and 990 cm$^{-1}$. The polymer contained 31.9% by weight bromine and 26.0% chlorine which is equivalent to 46.3 weight percent tetrabromoterephthalic acid anhydride and 52.4% tetrachloroterephthalic acid anhydride, i.e., a mole ratio of tetrabromoterephthalic acid moieties to tetrachloroterephthalic acid moieties of 1 to 1.83 compared to a feed ratio of 1 to 2. The acid number of the polymer was 32 mg of KOH per gram which was indicative of a molecular weight of about 3,500, and an average polymer chain containing 3.5 tetrabromoterephthalic acid moieties and 6.5 tetrachloroterephthalic acid moieties.

We claim:
1. The method of forming a tetrahaloterephthalic acid ester which comprises reacting a diacylium sulfate complex of a tetrahaloterephthalic acid with a hydroxy compound.
2. The method of claim 1, wherein said hydroxy compound is a glycol and a polyester is formed.
3. The process of claim 1, wherein the moiety of said complex is tetrabromoterephthalic acid.
4. The process of claim 1, wherein the acid moiety of said complex is tetrachloroterephthalic acid.
5. The process of claim 1, wherein said hydroxy compound is a monohydroxy compound.
6. The process of claim 5, wherein said monohydroxy compound is an alcohol containing from 1–24 carbon atoms.
7. The process of claim 5, wherein said monohydroxy compound is an aromatic hydroxy compound containing 6–24 carbon atoms.

* * * * *